USseparator005879908A

United States Patent [19]
Laping et al.

[11] Patent Number: 5,879,908
[45] Date of Patent: Mar. 9, 1999

[54] CRFG-1A, A TARGET AND MARKER FOR CHRONIC RENAL FAILURE

[75] Inventors: Nicholas J Laping, West Chester; Barbara Olson, Norristown; Yuan Zhu, Blue Bell, all of Pa.

[73] Assignee: Smithkline Beecham Corporation, Philadelphia, Pa.

[21] Appl. No.: 20,466

[22] Filed: Feb. 9, 1998

Related U.S. Application Data

[60] Provisional application No. 60/045,203, Apr. 30, 1997.
[51] Int. Cl.[6] .............................. C12P 21/06; C12N 1/20; C12N 15/00; C07H 17/00
[52] U.S. Cl. ..................... 435/69.1; 435/252.3; 435/325; 435/320.1; 536/23.1
[58] Field of Search ................................ 435/69.1, 252.3, 435/325, 320.1; 536/23.1

[56] References Cited

PUBLICATIONS

HGS EST #682636.

*Primary Examiner*—Karen Cochrane Carlson
*Attorney, Agent, or Firm*—Ratner & Prestia; William T. King; Elizabeth J. Hecht

[57] ABSTRACT

CRFG-1a polypeptides and polynucleotides and methods for producing such polypeptides by recombinant techniques are disclosed. Also disclosed are methods for utilizing CRFG-1a polypeptides and polynucleotides in the design of protocols for the treatment of chronic renal disease, renal ischemia, diabetic nephropathy, acute renal failure, Neurodegenerative disease, and Alzheimer's disease, among others, and diagnostic assays for such conditions.

10 Claims, No Drawings

CRFG-1A, A TARGET AND MARKER FOR CHRONIC RENAL FAILURE

This application claims the benefit of U.S. provisional application Ser. No. 60/045,203, filed Apr. 30, 1997, which is herein incorporated by reference in its entirety.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to GTP binding protein family, hereinafter referred to as chronic renal failure gene-1a (CRFG-1a). The invention also relates to inhibiting or activating the action of such polynucleotides and polypeptides.

BACKGROUND OF THE INVENTION

The sequence of CRFG-1a is similar to uncharacterized putative GTP binding proteins of yeast (YPL093w), Halobacterium cutirubrum and GTP1/OBG family of GTP binding proteins from Methanobacterium thermoautotrophicum. GTP binding proteins play important roles in intracellular transport, protein targeting and vesicle fusion.

This indicates that the GTP binding proteins fairly has an established, proven history as therapeutic targets. Clearly there is a need for identification and characterization of further members of GTP binding protein family which can play a role in preventing, ameliorating or correcting dysfunctions or diseases, including, but not limited to, chronic renal disease, renal ischemia, diabetic nephropathy, acute renal failure, Neurodegenerative disease, and Alzheimer's disease.

SUMMARY OF THE INVENTION

In one aspect, the invention relates to CRFG-1a polypeptides and recombinant materials and methods for their production. Another aspect of the invention relates to methods for using such CRFG-1a polypeptides and polynucleotides. Such uses include the treatment of chronic renal disease, renal ischemia, diabetic nephropathy, acute renal failure, Neurodegenerative disease, and Alzheimer's disease, among others. In still another aspect, the invention relates to methods to identify agonists and antagonists using the materials provided by the invention, and treating conditions associated with CRFG-1a imbalance with the identified compounds. Yet another aspect of the invention relates to diagnostic assays for detecting diseases associated with inappropriate CRFG-1a activity or levels.

DESCRIPTION OF THE INVENTION

Definitions

The following definitions are provided to facilitate understanding of certain terms used frequently herein.

"CRFG-1a" refers, among others, generally to a polypeptide having the amino acid sequence set forth in SEQ ID NO:2 or an allelic variant thereof.

"CRFG-1a activity or CRFG-1a polypeptide activity" or "biological activity of the CRFG-1a or CRFG-1a polypeptide" refers to the metabolic or physiologic function of said CRFG-1a including similar activities or improved activities or these activities with decreased undesirable side-effects. Also included are antigenic and immunogenic activities of said CRFG-1a.

"CRFG-1a gene" refers to a polynucleotide having the nucleotide sequence set forth in SEQ ID NO:1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Post-translational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology, Lesk,* A. M., ed., Oxford University Press, New York, 1988; *Biocomputing: Informatics and Genome Projects,* Smith, D. W., ed., Academic Press, New York, 1993; *Computer Analysis of Sequence Data,* Part I, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991; and Carillo, H., and Lipman, D., SIAM *J. Applied Math.,* 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215: 403–410 (1990). The well known Smith Waterman algorithm may also be used to determine identity.

Preferred parameters for polypeptide sequence comparison include the following:

1) Algorithm: Needleman and Wunsch, J. Mol Biol. 48: 443–453 (1970)

Comparison matrix: BLOSSUM62 from Hentikoff and Hentikoff, Proc. Natl. Acad. Sci. USA. 89:10915–10919 (1992)

Gap Penalty: 12

Gap Length Penalty: 4

A program useful with these parameters is publicly available as the "gap" program from Genetics Computer Group, Madison Wis. The aforementioned parameters are the default parameters for polypeptide comparisons (along with no penalty for end gaps).

Preferred parameters for polynucleotide comparison include the following:

1) Algorithm: Needleman and Wunsch, J. Mol Biol. 48: 443–453 (1970)

Comparison matrix: matches=+10, mismatch=0

Gap Penalty: 50

Gap Length Penalty: 3

A program useful with these parameters is publicly available as the "gap" program from Genetics Computer Group, Madison Wis. The aforementioned parameters are the default parameters for polynucleotide comparisons.

Preferred polynucleotide embodiments further include an isolated polynucleotide comprising a polynucleotide having at least a 50, 60, 70, 80, 85, 90, 95, 97 or 100% identity to a polynucleotide reference sequence of SEQ ID NO:1, wherein said reference sequence may be identical to the sequence of SEQ ID NO:1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:1 by the numerical percent of the respective percent identity and subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, and y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

Preferred polypeptide embodiments further include an isolated polypeptide comprising a polypeptide having at least a 50, 60, 70, 80, 85, 90, 95, 97 or 100% identity to a polypeptide reference sequence of SEQ ID NO:2, wherein said reference sequence may be identical to the sequence of SEQ ID NO:2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the numerical percent of the respective percent identity and subtracting that product from said total number of amino acids in SEQ ID NO:2, or:

$$n_a \leq x_a - (x_a \cdot y)$$

wherein $n_a$ is the number of amino acid alterations, $x_a$ is the total number of amino acids in SEQ ID NO:2, and y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and wherein any non-integer product of $x_a$ and y is rounded down to the nearest integer prior to subtracting it from $x_a$.

Polypeptides of the Invention

In one aspect, the present invention relates to CRFG-1a polypeptides (or CRFG-1a proteins). The CRFG-1a polypeptides include the polypeptide of SEQ ID NOS:2 and 4; as well as polypeptides comprising the amino acid sequence of SEQ ID NO:2; and polypeptides comprising the amino acid sequence which have at least 80% identity to that of SEQ ID NO:2 over its entire length, and still more preferably at least 90% identity, and even still more preferably at least 95% identity to SEQ ID NO:2. Furthermore, those with at least 97–99% are highly preferred. Also included within CRFG-1a polypeptides are polypeptides having the amino acid sequence which have at least 80% identity to the polypeptide having the amino acid sequence of SEQ ID NO:2 over its entire length, and still more preferably at least 90% identity, and still more preferably at least 95% identity to SEQ ID NO:2. Furthermore, those with at least 97–99% are highly preferred. Preferably CRFG-1a polypeptide exhibit at least one biological activity of CRFG-1a.

The CRFG-1a polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the CRFG-1a polypeptides are also included in the invention. A fragment is a polypeptide having an amino acid sequence that entirely is the same as part, but not all, of the amino acid sequence of the aforementioned CRFG-1a polypeptides. As with CRFG-1a polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of CRFG-1a polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of CRFG-1a polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate CRFG-1a activity, including those with a similar activity or an improved activity, or with a decreased undesirable activity. Also included are those that are antigenic or immunogenic in an animal, especially in a human.

Preferably, all of these polypeptide fragments retain the biological activity of the CRFG-1a, including antigenic activity. Among the most preferred fragment is that having the amino acid sequence of SEQ ID NO:4. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The CRFG-1a polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to CRFG-1a polynucleotides. CRFG-1a polynucleotides include isolated polynucleotides which encode the CRFG-1a polypeptides and fragments, and polynucleotides closely related thereto. More specifically, CRFG-1a polynucleotide of the invention include a polynucleotide comprising the nucleotide sequence contained in SEQ ID NO:1 encoding a CRFG-1a polypeptide of SEQ ID NO:2, and polynucleotides having the particular sequences of SEQ ID NOS:1 and 3. CRFG-1a polynucleotides further include a polynucleotide comprising a nucleotide sequence that has at least 80% identity over its entire length to a nucleotide sequence encoding the CRFG-1a polypeptide of SEQ ID NO:2, and a polynucleotide comprising a nucleotide sequence that is at least 80% identical to that of SEQ ID NO:1 over its entire length. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included under CRFG-1a polynucleotides are a nucleotide sequence which has sufficient identity to a nucleotide sequence contained in SEQ ID NO:1 to hybridize under conditions useable for amplification or for use as a probe or marker. The invention also provides polynucleotides which are complementary to such CRFG-1a polynucleotides.

CRFG-1a of the invention is structurally related to other proteins of the GTP binding protein family, as shown by the results of sequencing the cDNA encoding human CRFG-1a. The cDNA sequence of SEQ ID NO:1 contains an open reading frame (nucleotide number 3 to 1904) encoding a polypeptide of 634 amino acids of SEQ ID NO:2. The amino acid sequence of Table 1 (SEQ ID NO:2) has about 46.1% identity (using FASTA) in 634 amino acid residues with Hypothetical protein YPL093w from yeast (H. Bussey et al. Nature 387 (6632 Suppl), 103–105, 1997). The nucleotide sequence of Table 1 (SEQ ID NO:1) has about 59.7% identity (using FASTA) in 1351 nucleotide residues with *Saccharomyces cerevisiae* chromosome XVI cosmid 8059/8047 (H. Bussey et al. Nature 387 (6632 Suppl), 103–105, 1997). Thus, CRFG-1a polypeptides and polynucleotides of the present invention are expected to have, inter alia, similar biological functions/properties to their homologous polypeptides and polynucleotides, and their utility is obvious to anyone skilled in the art.

TABLE 1[a]

| | |
|---|---|
| AGCATGGCACATTACAACTTCAAGAAAATTACGGTGGTGC | 40 |
| CGTCCGCCAAGGACTTCATAGACCTCACGTTGTCCAAGAC | 80 |
| TCAACGAAAGACTCCAACCGTTATTCATAAACATTACCAA | 120 |
| ATACATCGCATTAGACATTTTTACATGAGAAAAGTCAAAT | 160 |
| TTACTCAACAGAATTACCATGATAGACTTTCACAAATTCT | 200 |
| AACAGATTTCCCCAAATTGGATGATATTCATCCGTTCTAT | 240 |
| GCTGATTTGATGAATATTCTCTACGACAAGGATCATTACA | 280 |
| AGTTGGCTCTGGGGCAAATAAATATTGCCAAAAATTTAGT | 320 |
| GGACAATGTTGCTAAAGATTATGTGCGACTGATGAAGTAT | 360 |
| GGCGACTCTCTCTACCGCTGCAAACAGCTGAAGCGTGCGG | 400 |
| CCCTGGGACGGATGTGCACAGTGATCAAGAGGCAGAAGCA | 440 |
| GAGTTTGGAGTATTTGGAGCAAGTGCGTCAGCATTTATCC | 480 |
| CGTTTGCCAACCATTGATCCGAATACCAGGACCCTGCTTT | 520 |
| TGTGTGGGTACCCAAATGTTGGGAAGTCCAGCTTCATCAA | 560 |
| CAAGGTGACGAGAGCAGACGTGGATGTCCAGCCCTATGCG | 600 |
| TTCACAACCAAGTCTCTGTTTGTTGGGCACATGGATTATA | 640 |
| AGTATCTACGTTGGCAGGTTGTAGACACTCCTGGGATCCT | 680 |
| GGACCACCCTCTGGAGGATAGGAACACCATCGAGATGCAG | 720 |
| GCCATCACTGCCCTGGCCCACCTCCGTGCTGCGGTCCTGT | 760 |

TABLE 1ª-continued

| | |
|---|---|
| ATGTGATGGATTTGTCTGAGCAGTGTGGGCATGGGCTGAG | 800 |
| GGAACAGCTAGAACTCTTCCAGAACATCAGACCTCTCTTC | 840 |
| ATCAACAAGCCTCTCATAGTTGTAGCCAACAAATGTGATG | 880 |
| TGAAGAGAATAGCTGAACTTTCTGAAGATGATCAGAAAAT | 920 |
| ATTTACAGATTTGCAGTCTGAAGGATTCCCTGTAATAGAG | 960 |
| ACCAGCACCCTGACTGAGGAAGGTGTTATTAAAGTTAAAA | 1000 |
| CAGAGGCTTGCGATAGGCTTTTGGCTCATCGAGTGGAAAC | 1040 |
| CAAAATGAAGGGAAATAAAGTGAATGAGGTGCTGAATAGA | 1080 |
| CTGCACCTGGCTATCCCAACCAGGAGGGACGATAAGGAGA | 1120 |
| GGCCCCCTTTCATCCCTGAAGGAGTGGTGGCTCGCAGGAA | 1160 |
| GAGGATGGAAACTGAGGAGTCCAGGAAGAAGAGGGAACGA | 1200 |
| GATCTTGAGCTGGAAATGGGAGATGATTATATTTTGGATC | 1240 |
| TTCAGAAGTACTGGGATTTAATGAATTTGTCTGAAAAACA | 1280 |
| TGATAAGATACCAGAAATCTGGGAAGGCCATAATATAGCT | 1320 |
| GATTATATTGATCCAGCCATCATGAAGAAATTGGAAGAAT | 1360 |
| TAGAAAAAGAAGAAGAGCTGAGAACAGCTGCTGGAGAGTA | 1400 |
| TGACAGTGTATCTGAGAGTGAAGACGAAGAGATGCTGGAA | 1440 |
| ATCCGACAGCTGGCAAAGCAAATTCGAGAGAAAAAGAAGT | 1480 |
| TGAAAATTCTGGAGTCCAAAGAAAAGAATACACAGGGACC | 1520 |
| CAGGATGCCGCGAACTGCTAAGAAGGTTCAGAGGACAGTT | 1560 |
| TTGGAGAAGGAGATGCGTAGTCTTGGTGTTGACATGGACG | 1600 |
| ATAAAGACGATGCCCATTACGCAGTCCAGGCAAGAAGATC | 1640 |
| CCGGAGCATCACTAGGAAAAGAAAGCGGGAAGACTCTGCT | 1680 |
| CCCCCGTCCTCTGTGGCCCGGAGTGGGAGTTGCTCTCGAA | 1720 |
| CTCCACGTGACGTTTCTGGTCTTAGGGATGTCAAGATGGT | 1760 |
| GAAGAAAGCCAAGACTATGATGAAGAATGCTCAGAAGAAG | 1800 |
| ATGAATCGGTTGGGGAAGAAAGGGGAGGCGGATAGACACG | 1840 |
| TGTTTGATATGAAGCCCAAGCACTTGCTGTCTGGGAAGAG | 1880 |

TABLE 1ª-continued

| | |
|---|---|
| GAAAGCTGGTAAAAAGGACAGGAGATAGTATCCGTTTGGT | 1920 |
| TGGCGTGGCTTCGCTAGAGTGTTGCTGTTTATTTCCTGTT | 1960 |
| TTGGCACAGTATGGTTTCATGAAATTGGAGCTCTGTATAA | 2000 |
| ACTGAAAAGACAAAATAAGTAAAGCACTTGTTGCTTTGC | 2040 |
| TGAAAACTATGGTTAACCCTATATAGGTGTGGGAAATTTT | 2080 |
| TGTCACTGCATAATATTACAAATATTTTGAGTAGACAGTG | 2120 |
| TTTCCACATTTAATGGAGTATCAGTTGCTTCAGATTTTCA | 2160 |
| GAACTGGGAAGATTTACTGGTGTAACTGGGTTGTTTTTGA | 2200 |
| TGGAGAAAAACCTTATTTTCTTTTGTAAGAGCTGGGAGCA | 2240 |
| AACACGTTTATGAGTGTGTCGGAATCCCGTGCTTAAAATA | 2280 |
| CGCTCTTAAATTATTTTCTAGTCTTATTTCACAATGTCTC | 2320 |
| ATTGTAGTCTGTCTTCAACTATTTTATCCAAAATANACCT | 2360 |
| CCAGAAGAAAG | 2371 |

ªA nucleotide sequence of a human CRFG-1a (SEQ ID NO: 1).

TABLE 2[b]

| | |
|---|---|
| M A H Y N F K K I T V V P S A K D F I D L T L S K T Q R K T P T V I H K H Y Q I | 40 |
| H R I R H F Y M R K V K F T Q Q N Y H D R L S Q I L T D F P K L D D I H P F Y A | 80 |
| D L M N I L Y D K D H Y K L A L G Q I N I A K N L V D N V A K D Y V R L M K Y G | 120 |
| D S L Y R C K Q L K R A A L G R M C T V I K R Q K Q S L E Y L E Q V R Q H L S R | 160 |
| L P T I D P N T R T L L L C G Y P N V G K S S F I N K V T R A D V D V Q P Y A F | 200 |
| T T K S L F V G H M D Y K Y L R W Q V V D T P G I L D H P L E D R N T I E M Q A | 240 |
| I T A L A H L R A A V L Y V M D L S E Q C G H G L R E Q L E L F Q N I R P L F I | 280 |
| N K P L I V V A N K C D V K R I A E L S E D D Q K I F T D L Q S E G F P V I E T | 320 |
| S T L T E E G V I K V K T E A C D R L L A H R V E T K M K G N K V N E V L N R L | 360 |
| H L A I P T R R D D K E R P P F I P E G V V A R R K R M E T E E S R K K R E R D | 400 |
| L E L E M G D D Y I L D L Q K Y W D L M N L S E K H D K I P E I W E G H N I A D | 440 |
| Y I D P A I M K K L E E L E K E E E L R T A A G E Y D S V S E S E D E E M L E I | 480 |

TABLE 2[b]-continued

R Q L A K Q I R E K K K L K I L E S K E K N T Q G P R M P R T A K K V Q R T V L  520

E K E M R S L G V D M D D K D D A H Y A V Q A R R S R S I T R K R K R E D S A P  560

P S S V A R S G S C S R T P R D V S G L R D V K M V K K A K T M M K N A Q K K M  600

N R L G K K G E A D R H V F D M K P K H L L S G K R K A G K K D R R  634

[b]An amino acid sequence of a human CRFG-1a(SEQ ID NO: 2).

One polynucleotide of the present invention encoding CRFG-1a may be obtained using standard cloning and screening, from a cDNA library derived from mRNA in cells of human kidney and testes using the expressed sequence tag (EST) analysis (Adams, M. D., et al. *Science* (1991) 252:1651–1656; Adams, M. D. et al., *Nature,* (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

The nucleotide sequence encoding CRFG-1a polypeptide of SEQ ID NO:2 may be identical to the polypeptide encoding sequence contained in Table 1 (nucleotide number 3 to 1904 of SEQ ID NO:1), or it may be a sequence, which as a result of the redundancy (degeneracy) of the genetic code, also encodes the polypeptide of SEQ ID NO:2.

When the polynucleotides of the invention are used for the recombinant production of CRFG-1a polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain non coding 5' and 3' sequences, such as transcribed, non-translated sequences, splicing and polyadenylation signals, ribosome binding sites and sequences that stabilize mRNA.

Further preferred embodiments are polynucleotides encoding CRFG-1a variants comprising the amino acid sequence of CRFG-1a polypeptide of Table 2 (SEQ ID NO:2) in which several, 5–10, 1–5, 1–3, 1–2 or 1 amino acid residues are substituted, deleted or added, in any combination. Among the preferred polynucleotides of the present invention is contained in Table 3 (SEQ ID NO:3) encoding the amino acid sequence of Table 4 (SEQ ID NO:4).

TABLE 3[c]

| | | | | |
|---|---|---|---|---|
| g ACTCTGCTC | CCCCGTCCTC | TGTGGCCCGG | Ag TGGGAGTT | |
| GCTCTCGAAC | TCCACGTGAC | GTTTCTGGTC | TTAGGGATGT | 80 |
| CAAg ATGGTG | AAg AAAGCCA | AGACTATGAT | GAAGAATGCT | |
| CAg AAg AAg A | TGAATCGGTT | GGGGAAg AAA | GGGGAGGCGG | 160 |
| ATATACACTT | g TTTGATATG | AAGCCCAAg C | ACTTGCTGTC | |
| TGGGAAg AGG | AAAGCTGGTa | AAAAGGACAG | GAGATAg TAT | 240 |
| CCGTTTGGTT | GGCGTGGCTT | CGCTAg Ag TG | TTGCTGTTTA | |
| TTTCCTGGTT | TGGCACAGTA | TGGTTTCa TG | AAATTGGAGC | 320 |
| TCTGTa TAAA | CTGAAAAAGA | CAAAATAAGT | AAAGCACTTG | |
| TTGCTTTGCT | GAAAACTATG | GTTAACCCTA | TATAGGTGTG | 400 |
| GGAAATTTTT | GTCa CTGCAT | AATATTACa A | ATATTCTGAG | |
| TAGACAGt GT | TTCCACATTT | AATGGAGTAT | CAGTTGCTTC | 480 |
| AGATTTTCAG | AACTGGGAAG | ATTTACTGGT | GTAACTGGGT | |
| TGTTTTTGAT | GGAGAAAAAC | CTTATTTTCT | TTTGTAAGAG | 560 |
| CTGGGAGCAA | ACACGTTTAT | GAGTGTGTCG | GAATCCCGTG | |
| CTTAAAATAC | GCTCTTAAAT | t ATTTTCTAG | TCCTTATTTT | 640 |
| ACAATGTCTC | ATTGTAGTCT | GTCTTCAACT | ATTTTATCCA | |
| AAATAAACCT | CCAGAAGGAA | AAAAAAAAAA | AAAAAA | 716 |

[c]A partial nucleotide sequence of a human CRFG-1a(SEQ ID NO: 3).

TABLE 4[d]

H E D K D D A H Y A V Q A R R S R S I T R K R K R E D S A P P S S V A R S G S C   40

S R T P R D V S G L R D V K M V K K A K T M M K N A Q K K M N R L G K K G E A D   80

I H L F D M K P K H L L S G K R K A G K K D R R   104

[d] A partial amino acid sequence of a human CRFG-1a(SEQ ID NO: 4).

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 80%, and preferably at least 90%, and more preferably at least 95%, yet even more preferably 97–99% identity between the sequences.

Polynucleotides of the invention, which are identical or sufficiently identical to a nucleotide sequence contained in SEQ ID NO:1 or a fragment thereof (including that of SEQ ID NO:3), may be used as hybridization probes for cDNA and genomic DNA, to isolate full-length cDNAs and genomic clones encoding CRFG-1a polypeptide and to isolate cDNA and genomic clones of other genes (including genes encoding homologs and orthologs from species other than human) that have a high sequence similarity to the CRFG-1a gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding CRFG-1a polypeptide, including homologs and orthologs from species other than human, comprises the steps of screening an appropriate library under stingent hybridization conditions with a labeled probe having the SEQ ID NO:1 or a fragment thereof (including that of SEQ ID NO:3), and isolating full-length cDNA and genomic clones containing said polynucleotide sequence. Such hybridization techniques are well known to those of skill in the art. Thus in another aspect, CRFG-1a polynucleotides of the present invention further include a nucleotide sequence comprising a nucleotide sequence that hybridize under stringent condition to a nucleotide sequence having SEQ ID NO:1 or a fragment thereof (including that of SEQ ID NO:3). Also included with CRFG-1a polypeptides are polypeptide comprising amino acid sequence encoded by nucleotide sequence obtained by the above hybridization condition. Stringent hybridization conditions are as defined above or, alternatively, conditions under overnight incubation at 42° C. in a solution comprising: 50% formamide, 5xSSC (150 mM NaCl, 15 mM trisodium citrate), 50 mM sodium phosphate (pH7.6), 5x Denhardt's solution, 10% dextran sulfate, and 20 microgram/ml denatured, sheared salmon sperm DNA, followed by washing the filters in 0.1x SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al, BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, E. coli, Streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the periplasmic space or into the extracellular environment, appropriate secretion signals may be incorporated into the desired polypeptide.

These signals may be endogenous to the polypeptide or they may be heterologous signals.

If the CRFG-1a polypeptide is to be expressed for use in screening assays, generally, it is preferred that the polypeptide be produced at the surface of the cell. In this event, the cells may be harvested prior to use in the screening assay. If CRFG-1a polypeptide is secreted into the medium, the medium can be recovered in order to recover and purify the polypeptide; if produced intracellularly, the cells must first be lysed before the polypeptide is recovered. CRFG-1a polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of CRFG-1a polynucleotides for use as diagnostic reagents. Detection of a mutated form of CRFG-1a gene associated with a dysfunction will provide a diagnostic tool that can add to or define a diagnosis of a disease or susceptibility to a disease which results from under-expression, over-expression or altered expression of CRFG-1a. Individuals carrying mutations in the CRFG-1a gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled CRFG-1a nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985)230:1242. Sequence changes at specific locations may also be revealed by nuclease protection assays, such as RNase and S1 protection or the chemical cleavage method. See Cotton et al., *Proc Natl Acad Sci USA* (1985)85: 4397–4401. In another embodiment, an array of oligonucleotides probes comprising CRFG-1a nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., *Science*, Vol 274, pp 610–613 (1996)).

The diagnostic assays offer a process for diagnosing or determining a susceptibility to chronic renal disease, renal ischemia, diabetic nephropathy, acute renal failure, Neurodegenerative disease, and Alzheimer's disease through detection of mutation in the CRFG-1a gene by the methods described.

In addition, chronic renal disease, renal ischemia, diabetic nephropathy, acute renal failure, Neurodegenerative disease, and Alzheimer's disease, can be diagnosed by methods comprising determining from a sample derived from a subject an abnormally decreased or increased level of CRFG-1a polypeptide or CRFG-1a mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an CRFG-1a polypeptide, in a sample derived from a host are well-known to those of skill in the art. Such assay methods include radioimmunoassays, competitive-binding assays, Western Blot analysis and ELISA assays.

Thus in another aspect, the present invention relates to a diagonostic kit for a disease or suspectability to a disease, particularly chronic renal disease, renal ischemia, diabetic nephropathy, acute renal failure, Neurodegenerative disease, and Alzheimer's disease, which comprises:

(a) a CRFG-1a polynucleotide, preferably the nucleotide sequence of SEQ ID NO:1, or a fragment thereof;

(b) a nucleotide sequence complementary to that of (a);

(c) a CRFG-1a polypeptide, preferably the polypeptide of SEQ ID NO:2, or a fragment thereof; or (d) an antibody to a CRFG-1a polypeptide, preferably to the polypeptide of SEQ ID NO:2.

It will be appreciated that in any such kit, (a), (b), (c) or (d) may comprise a substantial component.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes). The differences in the cDNA or genomic sequence between affected and unaffected individuals can also be determined. If a mutation is observed in some or all of the affected individuals but not in any normal individuals, then the mutation is likely to be the causative agent of the disease.

The CRFG-1a gene (SEQ ID NO:1) is found on chromosome 10p15.2–15.3 which is associated with glioma of the brain.

Antibodies

The polypeptides of the invention or their fragments or analogs thereof, or cells expressing them can also be used as immunogens to produce antibodies inmunospecific for the CRFG-1a polypeptides. The term "immunospecific" means that the antibodies have substantiall greater affinity for the polypeptides of the invention than their affinity for other related polypeptides in the prior art.

Antibodies generated against the CRFG-1a polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al, *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against CRFG-1a polypeptides may also be employed to treat chronic renal disease, renal ischemia, diabetic nephropathy, acute renal failure, Neurodegenerative disease, and Alzheimer's disease, among others.

Vaccines

Another aspect of the invention relates to a method for inducing an immunological response in a mammal which comprises inoculating the mammal with CRFG-1a polypeptide, or a fragment thereof, adequate to produce antibody and/or T cell immune response to protect said animal from chronic renal disease, renal ischemia, diabetic nephropathy, acute renal failure, Neurodegenerative disease, and Alzheimer's disease, among others. Yet another aspect of the invention relates to a method of inducing immunological response in a mammal which comprises, delivering CRFG-1a polypeptide via a vector directing expression of CRFG-1a polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that manual to a CRFG-1a polypeptide wherein the composition comprises a CRFG-1a polypeptide or CRFG-1a gene. The vaccine formulation may further comprise a suitable carrier. Since CRFG-1a polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain antioxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The CRFG-1a polypeptide of the present invention may be employed in a screening process for compounds which activate (agonists) or inhibit activation of (antagonists, or otherwise called inhibitors) the CRFG-1a polypeptide of the present invention. Thus, polypeptides of the invention may also be used to assess identify agonist or antagonists from, for example, cells, cell-free preparations, chemical libraries, and natural product mixtures. These agonists or antagonists may be natural or modified substrates, ligands, enzymes, receptors, etc., as the case may be, of the polypeptide of the present invention; or may be structural or functional mimetics of the polypeptide of the present invention. See Coligan et al., *Current Protocols in Immunology* 1(2):Chapter 5 (1991).

CRFG-1a polypeptides are responsible for many biological functions, including many pathologies. Accordingly, it is desirous to find compounds and drugs which stimulate CRFG-1a polypeptide on the one hand and which can inhibit the function of CRFG-1a polypeptide on the other hand. In general, agonists are employed for therapeutic and prophylactic purposes for such conditions as chronic renal disease, renal ischemia, diabetic nephropathy, acute renal failure, Neurodegenerative disease, and Alzheimer's disease. Antagonists may be employed for a variety of therapeutic and prophylactic purposes for such conditions as chronic renal disease, renal ischemia, diabetic nephropathy, acute renal failure, Neurodegenerative disease, and Alzheimer's disease.

In general, such screening procedures may involve using appropriate cells which express the CRFG-1a polypeptide or respond to CRFG-1a polypeptide of the present invention. Such cells include cells from mammals, yeast, Drosophila or *E. coli*. Cells which express the CRFG-1a polypeptide (or cell membrane containing the expressed polypeptide) or respond to CRFG-1a polypeptide are then contacted with a test compound to observe binding, or stimulation or inhibition of a functional response. The ability of the cells which were contacted with the candidate compounds is compared with the same cells which were not contacted for CRFG-1a activity.

The assays may simply test binding of a candidate compound wherein adherence to the cells bearing the CRFG-1a polypeptide is detected by means of a label directly or indirectly associated with the candidate compound or in an assay involving competition with a labeled competitor. Further, these assays may test whether the candidate compound results in a signal generated by activation of the CRFG-1a polypeptide, using detection systems appropriate to the cells bearing the CRFG-1a polypeptide. Inhibitors of activation are generally assayed in the presence of a known agonist and the effect on activation by the agonist by the presence of the candidate compound is observed.

Further, the assays may simply comprise the steps of mixing a candidate compound with a solution containing a CRFG-1a polypeptide to form a mixture, measuring CRFG-1a activity in the mixture, and comparing the CRFG-1a activity of the mixture to a standard.

The CRFG-1a cDNA, protein and antibodies to the protein may also be used to configure assays for detecting the effect of added compounds on the production of CRFG-1a mRNA and protein in cells. For example, an ELISA may be constructed for measuring secreted or cell associated levels of CRFG-1a protein using monoclonal and polyclonal antibodies by standard methods known in the art, and this can be used to discover agents which may inhibit or enhance the production of CRFG-1a (also called antagonist or agonist, respectively) from suitably manipulated cells or tissues.

The CRFG-1a protein may be used to identify membrane bound or soluble receptors, if any, through standard receptor binding techniques known in the art. These include, but are not limited to, ligand binding and crosslinking assays in which the CRFG-1a is labeled with a radioactive isotope (eg 125I), chemically modified (eg biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. In addition to being used for purification and cloning of the receptor, these binding assays can be used to identify agonists and antagonists of CRFG-1a which compete with the binding of CRFG-1a to its receptors, if any. Standard methods for conducting screening assays are well understood in the art.

Examples of potential CRFG-1a polypeptide antagonists include antibodies or, in some cases, oligonucleotides or proteins which are closely related to the ligands, substrates, enzymes, receptors, etc., as the case may be, of the CRFG-1a polypeptide, e.g., a fragment of the ligands, substrates, enzymes, receptors, etc.; or small molecules which bind to the polypeptide of the present invention but do not elicit a response, so that the activity of the polypeptide is prevented.

Thus in another aspect, the present invention relates to a screening kit for identifying agonists, antagonists, ligands, receptors, substrates, enzymes, etc. for CRFG-1a polypeptides; or compounds which decrease or enhance the production of CRFG-1a polypeptides, which comprises:

(a) a CRFG-1a polypeptide, preferably that of SEQ ID NO:2;

(b) a recombinant cell expressing a CRFG-1a polypeptide, preferably that of SEQ ID NO:2;

(c) a cell membrane expressing a CRFG-1a polypeptide; preferably that of SEQ ID NO:2; or (d) antibody to a CRFG-1a polypeptide, preferably that of SEQ ID NO:2.

It will be appreciated that in any such kit, (a), (b), (c) or (d) may comprise a substantial component.

Prophylactic and Therapeutic Methods

This invention provides methods of treating abnormal conditions such as, chronic renal disease, renal ischemia, diabetic nephropathy, acute renal failure, Neurodegenerative disease, and Alzheimer's disease, related to both an excess of and insufficient amounts of CRFG-1a polypeptide activity.

If the activity of CRFG-1a polypeptide is in excess, several approaches are available. One approach comprises administering to a subject an inhibitor compound (antagonist) as hereinabove described along with a pharmaceutically acceptable carrier in an amount effective to inhibit the function of the CRFG-1a polypeptide, such as, for example, by blocking the binding of ligands, substrates, enzymes, receptors, etc., or by inhibiting a second signal, and thereby alleviating the abnormal condition. In another approach, soluble forms of CRFG-1a polypeptides still capable of binding the ligand, substrate, enzymes, receptors, etc. in competition with endogenous CRFG-1a polypeptide may be administered. Typical embodiments of such competitors comprise fragments of the CRFG-1a polypeptide.

In another approach, soluble forms of CRFG-1a polypeptides still capable of binding the ligand in competition with endogenous CRFG-1a polypeptide may be administered. Typical embodiments of such competitors comprise fragments of the CRFG-1a polypeptide.

In still another approach, expression of the gene encoding endogenous CRFG-1a polypeptide can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988)241:456; Dervan et al., *Science* (1991)251:1360. These oligomers can be administered per se or the relevant oligomers can be expressed in vivo.

For treating abnormal conditions related to an under expression of CRFG-1a and its activity, several approaches are also available. One approach comprises administering to a subject a therapeutically effective amount of a compound which activates CRFG-1a polypeptide, i.e., an agonist as described above, in combination with a pharmaceutically acceptable carrier, to thereby alleviate the abnormal condition. Alternatively, gene therapy may be employed to effect the endogenous production of CRFG-1a by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996). Another approach is to administer a therapeutic amount of CRFG-1a polypeptides in combination with a suitable pharmaceutical carrier.

Formulation and Administration

Peptides, such as the soluble form of CRFG-1a polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used.

Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 μg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

Two animal model systems have been studied to provide targets for intervention in chronic renal failure. CRFG-1a is a novel gene identified by differential display PCR to be down regulated in three animal models of chronic renal failure, the obese Zucker rat and the ⅚ nephrectomized rat. In addition, aged Fisher 344 rats (24 months old), which have enlarged kidneys and reduced renal function, also have decreased expression of CRFG-1a. Loss of expression of this gene in renal failure may indicate an important role in normal functioning of the kidney.

In 5-month old obese Zucker rats, that have developed chronic renal failure, CRFG-1a mRNA is decreased to less than ⅓ of levels seen in lean and healthy age-matched controls. Because there is no correlation of proteinuria with CRFG-1a expression, a decrease in CRFG-1a is an early marker of renal impairment before standard clinical indicators.

While in the rat, CRFG-1a has 2 mRNA sizes of 2.5 and 1.5 kb, in the human only one molecular weight species is identified at 2.7 kb. Human CRFG-1a was mapped to human chromosome 10p15.2–15. This region of chromosome 10 is linked to 171840 PHOSPHOFRUCTOKINASE, PLATELET TYPE, 600449 DIHYDRODIOL DEHYDROGENASE, TYPE I; 601070 INTERLEUKIN-15 RECEPTOR, ALPHA; 600448 PROTEIN KINASE C, THETA FORM; 147270 INTER-ALPHA-TRYPSIN INHIBITOR, HEAVY CHAIN-1; 176870 PROTEIN HC; 137800 GLIOMA OF BRAIN, 300007 INTERLEUKIN-9 RECEPTOR; and 147680 INTERLEUKIN-2.

Normal mRNA expression on a multiple tissue northern blot identifies expression in skeletal muscle>testes>pancreas>heart>thymus>placenta>kidney>leukocytes>spleen>ovary>colon>brain>prostate.

EXAMPLE 1

The existence of CRFG-1a was determined by differential display polymerase chain reaction (DDPCR) as developed by Liang P. and Pardee A. B. *Science*. 1992 Aug. 14; Volume 257, pages 967–71. An oligonucleotide primer (Primer I), 5'-ACCACACATCTGA-3' (SEQ ID NO :5) was used in the synthesis of complementary DNA (cDNA) from RNA of lean and obese Zucker rat kidneys. cDNA was synthesized in a 20 μl volume with 0.5 μg RNA, 1 μM primer I, 20 μM dNTP, 400 units M-MLV reverse transcriptase (Promega, Madison, Wis.), and 1X standard reverse transcriptase buffer as given by the manufacturer. The reaction sample was heated to 65 degrees C. for 5 minutes and then incubated at 42 degrees C. for one hour. Polymerase chain reaction (PCR) was then performed in a 20 μl reaction volume using 4 μl of the cDNA synthesis reaction from above with 1.5 mM $MgCl_2$, 20 μM dNTP, 1 μM primer I, 1 μM primer II (5'-TGTTGGGAACAAG-3') (SEQ ID NO:6), 2 μCi [33-P]-d-alpha-ATP, 1.25 U Amplitaq polymerase (Perkin Elmer, Foster City, Calif.) and 1X standard PCR buffer from the manufacturer. PCR cycling conditions were 40 cycles of 94° C. for 30 seconds, 42° C. for 2 minutes, 72° C. for 30 seconds with a final extension of 72° C. for 5 minutes. Labeled PCR fragments from lean and obese Zucker rat Kidney RNA were resolved on a 12% SDS-polyacrylamide gel and exposed to X-ray film for 16 hours. A PCR amplified DNA fragment of 225 nucleotides was identified to be decreased in obese Zucker rat kidneys compared to lean age matched control rats. The fragment was excised from the dried polyacrylamide gel and DNA was eluted with boiling water. The eluted DNA was subjected to PCR using the same conditions as above. A 2 μl aliquot of the PCR reaction was then used to subclone the PCR fragment into the pCRII vector (Invitrogen, Carlsbad, Calif.) using standard reaction conditions of the manufacturer. The cDNA insert was then sequenced with the fmol sequencing kit (Promega, Madison, Wash.).

The sequence information was used to generate an antisense primer for the cloning of additional 5' sequence using the Marathon RACE kit (Clonetech, Palo, Alto, Calif.). The 607 nucleotide sequence obtained from the Marathon RACE kit was then used to identify the human homologue using the BLAST sequence analysis algorithm. The fall length human cDNA was cloned from kidney mRNA using the Marathon Race kit. The human sequence is given in SEQ ID NO:1.

EXAMPLE 2

CRFG-1a mRNA was detected by northern blot in RNA from rat kidneys. Total RNA was extracted from renal cortex by guanidinium thiocyanate denaturation and acidified phenol-chloroform extraction (CHOMCZYNSKI P, SACCHI N: *Analyt Biochem* 162:156–159, 1987). Total RNA (10 μg) was fractionated on 0.2M formaldehyde-1% agarose gels and transferred to nylon membranes (Nylon-1, Gibco-BRL, Gaithersburg, Md.) in 4X standard saline citrate. Equivalent loading and transfer were verified by methylene blue staining. Antisense [32P]cDNA probes were made for CRFG-1a that recognizes mRNA from rat at 1.5 and 2.5 kb. Northern blot analysis showed that CRFG-1a mRNA was decreased in kidneys from obese Zucker rats which develop renal failure. CRFG-1a mRNA was also decreased in kidneys after partial nephrectomy where ⅚ of the total renal mass was removed. This animal model develops chronic renal disease (Shea S M, Raskova J, Morrison A B *Am J Pathol* 1980 August; 100(2):513–528). CRFG-1a mRNA was also decreased in kidneys of aging F344 rats. F344 rats develop renal disease with advancing age (McDermott G F, Ingram A, Scholey J, Kirkland J L, Whiteside C I *J Gerontol A Biol Sci Med Sci* 1996 March; 51(2):M80–M85), suggesting that CRFG-1a is decreased in renal disease.

All publications, including but not limited to patents and patent applications, cited in this specification are herein incorporated by reference as if each individual publication were specifically and individually indicated to be incorporated by reference herein as though fully set forth.

What is claimed is:

1. An isolated polynucleotide comprising a nucleotide sequence that has at least 80% identity over its entire length to a nucleotide sequence encoding the CRFG-1a polypeptide of SEQ ID NO:2; or a nucleotide sequence complementary to said isolated polynucleotide.

2. The polynucleotide of claim 1 wherein said polynucleotide comprises the nucleotide sequence contained in SEQ ID NO:1 encoding the CRFG-1a polypeptide of SEQ ID NO2.

3. The polynucleotide of claim 1 wherein said polynucleotide comprises a nucleotide sequence that is at least 80% identical to that of SEQ ID NO:1 over its entire length.

4. The polynucleotide of claim 3 which is polynucleotide of SEQ ID NO:1.

5. The polynucleotide of claim 1 which is DNA or RNA.

6. An isolated DNA or RNA molecule comprising an expression system, wherein said expression system is capable of producing a CRFG-1a polypeptide comprising an amino acid sequence, which has at least 80% identity with the polypeptide of SEQ ID NO:2 when said expression system is present in a compatible host cell.

7. A host cell comprising the expression system of claim 6.

8. A recombinant host cell produced by a method of claim 1 or a membrane thereof expressing a CRFG-1a polypeptide.

9. A process for producing a cell which produces a CRFG-1a polypeptide thereof comprising transforming or transfecting a host cell with the expression system of claim 6 such that the host cell, under appropriate culture conditions, produces a CRFG-1a polypeptide.

10. A process for producing a CRFG-1a polypeptide comprising culturing a host of claim 7 under conditions sufficient for the production of said polypeptide and recovering the polypeptide from the culture.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 2371 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
AGCATGGCAC  ATTACAACTT  CAAGAAAATT  ACGGTGGTGC  CGTCCGCCAA  GGACTTCATA      60
GACCTCACGT  TGTCCAAGAC  TCAACGAAAG  ACTCCAACCG  TTATTCATAA  ACATTACCAA     120
ATACATCGCA  TTAGACATTT  TTACATGAGA  AAAGTCAAAT  TTACTCAACA  GAATTACCAT     180
GATAGACTTT  CACAAATTCT  AACAGATTTC  CCCAAATTGG  ATGATATTCA  TCCGTTCTAT     240
GCTGATTTGA  TGAATATTCT  CTACGACAAG  GATCATTACA  AGTTGGCTCT  GGGGCAAATA     300
AATATTGCCA  AAAATTTAGT  GGACAATGTT  GCTAAAGATT  ATGTGCGACT  GATGAAGTAT     360
GGCGACTCTC  TCTACCGCTG  CAAACAGCTG  AAGCGTGCGG  CCCTGGGACG  GATGTGCACA     420
GTGATCAAGA  GGCAGAAGCA  GAGTTTGGAG  TATTTGGAGC  AAGTGCGTCA  GCATTATCC      480
CGTTTGCCAA  CCATTGATCC  GAATACCAGG  ACCCTGCTTT  TGTGTGGGTA  CCCAAATGTT     540
GGGAAGTCCA  GCTTCATCAA  CAAGGTGACG  AGAGCAGACG  TGGATGTCCA  GCCCTATGCG     600
TTCACAACCA  AGTCTCTGTT  TGTTGGGCAC  ATGGATTATA  AGTATCTACG  TTGGCAGGTT     660
GTAGACACTC  CTGGGATCCT  GGACCACCCT  CTGGAGGATA  GGAACACCAT  CGAGATGCAG     720
GCCATCACTG  CCCTGGCCCA  CCTCCGTGCT  GCGGTCCTGT  ATGTGATGGA  TTTGTCTGAG     780
CAGTGTGGGC  ATGGGCTGAG  GGAACAGCTA  GAACTCTTCC  AGAACATCAG  ACCTCTCTTC     840
ATCAACAAGC  CTCTCATAGT  TGTAGCCAAC  AAATGTGATG  TGAAGAGAAT  AGCTGAACTT     900
TCTGAAGATG  ATCAGAAAAT  ATTTACAGAT  TTGCAGTCTG  AAGGATTCCC  TGTAATAGAG     960
ACCAGCACCC  TGACTGAGGA  AGGTGTTATT  AAAGTTAAAA  CAGAGGCTTG  CGATAGGCTT    1020
TTGGCTCATC  GAGTGGAAAC  CAAAATGAAG  GGAAATAAAG  TGAATGAGGT  GCTGAATAGA    1080
CTGCACCTGG  CTATCCCAAC  CAGGAGGGAC  GATAAGGAGA  GGCCCCCTTT  CATCCCTGAA    1140
GGAGTGGTGG  CTCGCAGGAA  GAGGATGGAA  ACTGAGGAGT  CCAGGAAGAA  GAGGGAACGA    1200
GATCTTGAGC  TGGAAATGGG  AGATGATTAT  ATTTGGATC   TTCAGAAGTA  CTGGGATTTA    1260
ATGAATTTGT  CTGAAAAACA  TGATAAGATA  CCAGAAATCT  GGGAAGGCCA  TAATATAGCT    1320
GATTATATTG  ATCCAGCCAT  CATGAAGAAA  TTGGAAGAAT  TAGAAAAAGA  AGAAGAGCTG    1380
AGAACAGCTG  CTGGAGAGTA  TGACAGTGTA  TCTGAGAGTG  AAGACGAAGA  GATGCTGGAA    1440
ATCCGACAGC  TGGCAAAGCA  AATTCGAGAG  AAAAAGAAGT  TGAAAATTCT  GGAGTCCAAA    1500
GAAAAGAATA  CACAGGGACC  CAGGATGCCG  CGAACTGCTA  AGAAGGTTCA  GAGGACAGTT    1560
TTGGAGAAGG  AGATGCGTAG  TCTTGGTGTT  GACATGGACG  ATAAAGACGA  TGCCCATTAC    1620
GCAGTCCAGG  CAAGAAGATC  CCGGAGCATC  ACTAGGAAAA  GAAAGCGGGA  AGACTCTGCT    1680
CCCCCGTCCT  CTGTGGCCCG  GAGTGGGAGT  TGCTCTCGAA  CTCCACGTGA  CGTTCTGGT     1740
CTTAGGGATG  TCAAGATGGT  GAAGAAAGCC  AAGACTATGA  TGAAGAATGC  TCAGAAGAAG    1800
```

```
ATGAATCGGT  TGGGGAAGAA  AGGGGAGGCG  GATAGACACG  TGTTTGATAT  GAAGCCCAAG    1860
CACTTGCTGT  CTGGGAAGAG  GAAAGCTGGT  AAAAAGGACA  GGAGATAGTA  TCCGTTTGGT    1920
TGGCGTGGCT  TCGCTAGAGT  GTTGCTGTTT  ATTTCCTGTT  TTGGCACAGT  ATGGTTTCAT    1980
GAAATTGGAG  CTCTGTATAA  ACTGAAAAAG  ACAAATAAG   TAAAGCACTT  GTTGCTTTGC    2040
TGAAAACTAT  GGTTAACCCT  ATATAGGTGT  GGGAAATTTT  TGTCACTGCA  TAATATTACA    2100
AATATTTTGA  GTAGACAGTG  TTTCCACATT  TAATGGAGTA  TCAGTTGCTT  CAGATTTTCA    2160
GAACTGGGAA  GATTTACTGG  TGTAACTGGG  TTGTTTTTGA  TGGAGAAAAA  CCTTATTTTC    2220
TTTTGTAAGA  GCTGGGAGCA  AACACGTTTA  TGAGTGTGTC  GGAATCCCGT  GCTTAAAATA    2280
CGCTCTTAAA  TTATTTTCTA  GTCTTATTTC  ACAATGTCTC  ATTGTAGTCT  GTCTTCAACT    2340
ATTTTATCCA  AAATANACCT  CCAGAAGAAA  G                                    2371
```

( 2 ) INFORMATION FOR SEQ ID NO:2:

( i ) SEQUENCE CHARACTERISTICS:
        ( A ) LENGTH: 634 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met  Ala  His  Tyr  Asn  Phe  Lys  Lys  Ile  Thr  Val  Val  Pro  Ser  Ala  Lys
 1                  5                     10                      15

Asp  Phe  Ile  Asp  Leu  Thr  Leu  Ser  Lys  Thr  Gln  Arg  Lys  Thr  Pro  Thr
               20                    25                     30

Val  Ile  His  Lys  His  Tyr  Gln  Ile  His  Arg  Ile  Arg  His  Phe  Tyr  Met
          35                       40                     45

Arg  Lys  Val  Lys  Phe  Thr  Gln  Gln  Asn  Tyr  His  Asp  Arg  Leu  Ser  Gln
 50                       55                      60

Ile  Leu  Thr  Asp  Phe  Pro  Lys  Leu  Asp  Asp  Ile  His  Pro  Phe  Tyr  Ala
 65                  70                      75                          80

Asp  Leu  Met  Asn  Ile  Leu  Tyr  Asp  Lys  Asp  His  Tyr  Lys  Leu  Ala  Leu
                    85                      90                     95

Gly  Gln  Ile  Asn  Ile  Ala  Lys  Asn  Leu  Val  Asp  Asn  Val  Ala  Lys  Asp
                    100                     105                    110

Tyr  Val  Arg  Leu  Met  Lys  Tyr  Gly  Asp  Ser  Leu  Tyr  Arg  Cys  Lys  Gln
          115                     120                    125

Leu  Lys  Arg  Ala  Ala  Leu  Gly  Arg  Met  Cys  Thr  Val  Ile  Lys  Arg  Gln
     130                     135                    140

Lys  Gln  Ser  Leu  Glu  Tyr  Leu  Glu  Gln  Val  Arg  Gln  His  Leu  Ser  Arg
145                      150                     155                     160

Leu  Pro  Thr  Ile  Asp  Pro  Asn  Thr  Arg  Thr  Leu  Leu  Leu  Cys  Gly  Tyr
               165                     170                     175

Pro  Asn  Val  Gly  Lys  Ser  Ser  Phe  Ile  Asn  Lys  Val  Thr  Arg  Ala  Asp
               180                     185                     190

Val  Asp  Val  Gln  Pro  Tyr  Ala  Phe  Thr  Thr  Lys  Ser  Leu  Phe  Val  Gly
          195                     200                     205

His  Met  Asp  Tyr  Lys  Tyr  Leu  Arg  Trp  Gln  Val  Val  Asp  Thr  Pro  Gly
     210                     215                     220

Ile  Leu  Asp  His  Pro  Leu  Glu  Asp  Arg  Asn  Thr  Ile  Glu  Met  Gln  Ala
225                      230                     235                     240

Ile  Thr  Ala  Leu  Ala  His  Leu  Arg  Ala  Ala  Val  Leu  Tyr  Val  Met  Asp
                    245                     250                     255
```

```
Leu  Ser  Glu  Gln  Cys  Gly  His  Gly  Leu  Arg  Glu  Gln  Leu  Glu  Leu  Phe
               260                 265                      270

Gln  Asn  Ile  Arg  Pro  Leu  Phe  Ile  Asn  Lys  Pro  Leu  Ile  Val  Val  Ala
               275                 280                      285

Asn  Lys  Cys  Asp  Val  Lys  Arg  Ile  Ala  Glu  Leu  Ser  Glu  Asp  Asp  Gln
          290                 295                      300

Lys  Ile  Phe  Thr  Asp  Leu  Gln  Ser  Glu  Gly  Phe  Pro  Val  Ile  Glu  Thr
305                      310                 315                           320

Ser  Thr  Leu  Thr  Glu  Glu  Gly  Val  Ile  Lys  Val  Lys  Thr  Glu  Ala  Cys
                    325                 330                           335

Asp  Arg  Leu  Leu  Ala  His  Arg  Val  Glu  Thr  Lys  Met  Lys  Gly  Asn  Lys
               340                 345                      350

Val  Asn  Glu  Val  Leu  Asn  Arg  Leu  His  Leu  Ala  Ile  Pro  Thr  Arg  Arg
          355                 360                      365

Asp  Asp  Lys  Glu  Arg  Pro  Pro  Phe  Ile  Pro  Glu  Gly  Val  Val  Ala  Arg
     370                 375                      380

Arg  Lys  Arg  Met  Glu  Thr  Glu  Glu  Ser  Arg  Lys  Lys  Arg  Glu  Arg  Asp
385                      390                 395                           400

Leu  Glu  Leu  Glu  Met  Gly  Asp  Asp  Tyr  Ile  Leu  Asp  Leu  Gln  Lys  Tyr
                    405                 410                           415

Trp  Asp  Leu  Met  Asn  Leu  Ser  Glu  Lys  His  Asp  Lys  Ile  Pro  Glu  Ile
               420                 425                      430

Trp  Glu  Gly  His  Asn  Ile  Ala  Asp  Tyr  Ile  Asp  Pro  Ala  Ile  Met  Lys
          435                 440                      445

Lys  Leu  Glu  Glu  Leu  Glu  Lys  Glu  Glu  Glu  Leu  Arg  Thr  Ala  Ala  Gly
     450                 455                      460

Glu  Tyr  Asp  Ser  Val  Ser  Glu  Ser  Glu  Asp  Glu  Glu  Met  Leu  Glu  Ile
465                      470                 475                           480

Arg  Gln  Leu  Ala  Lys  Gln  Ile  Arg  Glu  Lys  Lys  Lys  Leu  Lys  Ile  Leu
               485                 490                      495

Glu  Ser  Lys  Glu  Lys  Asn  Thr  Gln  Gly  Pro  Arg  Met  Pro  Arg  Thr  Ala
          500                 505                      510

Lys  Lys  Val  Gln  Arg  Thr  Val  Leu  Glu  Lys  Glu  Met  Arg  Ser  Leu  Gly
     515                 520                      525

Val  Asp  Met  Asp  Asp  Lys  Asp  Ala  His  Tyr  Ala  Val  Gln  Ala  Arg
530                      535                 540

Arg  Ser  Arg  Ser  Ile  Thr  Arg  Lys  Arg  Lys  Arg  Glu  Asp  Ser  Ala  Pro
545                      550                 555                           560

Pro  Ser  Ser  Val  Ala  Arg  Ser  Gly  Ser  Cys  Ser  Arg  Thr  Pro  Arg  Asp
                    565                 570                           575

Val  Ser  Gly  Leu  Arg  Asp  Val  Lys  Met  Val  Lys  Lys  Ala  Lys  Thr  Met
               580                 585                      590

Met  Lys  Asn  Ala  Gln  Lys  Met  Asn  Arg  Leu  Gly  Lys  Lys  Gly  Glu
          595                 600                      605

Ala  Asp  Arg  His  Val  Phe  Asp  Met  Lys  Pro  Lys  His  Leu  Leu  Ser  Gly
     610                 615                      620

Lys  Arg  Lys  Ala  Gly  Lys  Lys  Asp  Arg  Arg
625                      630
```

( 2 ) INFORMATION FOR SEQ ID NO:3:

( i ) SEQUENCE CHARACTERISTICS:
        ( A ) LENGTH: 716 base pairs
        ( B ) TYPE: nucleic acid
        ( C ) STRANDEDNESS: single (D) TOPOLOGY: linear (i i) MOLECULE TYPE: cDNA (x i) SEQUENCE DESCRIPTION: SEQ ID NO:3:

| GACTCTGCTC | CCCCGTCCTC | TGTGGCCCGG | AGTGGGAGTT | GCTCTCGAAC | TCCACGTGAC | 60 |
| GTTTCTGGTC | TTAGGGATGT | CAAGATGGTG | AAGAAAGCCA | AGACTATGAT | GAAGAATGCT | 120 |
| CAGAAGAAGA | TGAATCGGTT | GGGGAAGAAA | GGGGAGGCGG | ATATACACTT | GTTTGATATG | 180 |
| AAGCCCAAGC | ACTTGCTGTC | TGGGAAGAGG | AAAGCTGGTA | AAAAGGACAG | GAGATAGTAT | 240 |
| CCGTTTGGTT | GGCGTGGCTT | CGCTAGAGTG | TTGCTGTTTA | TTTCCTGGTT | TGGCACAGTA | 300 |
| TGGTTTCATG | AAATTGGAGC | TCTGTATAAA | CTGAAAAAGA | CAAAATAAGT | AAAGCACTTG | 360 |
| TTGCTTTGCT | GAAAACTATG | GTTAACCCTA | TATAGGTGTG | GGAAATTTTT | GTCACTGCAT | 420 |
| AATATTACAA | ATATTCTGAG | TAGACAGTGT | TTCCACATTT | AATGGAGTAT | CAGTTGCTTC | 480 |
| AGATTTTCAG | AACTGGGAAG | ATTTACTGGT | GTAACTGGGT | TGTTTTTGAT | GGAGAAAAAC | 540 |
| CTTATTTTCT | TTTGTAAGAG | CTGGGAGCAA | ACACGTTTAT | GAGTGTGTCG | GAATCCCGTG | 600 |
| CTTAAAATAC | GCTCTTAAAT | TATTTTCTAG | TCCTTATTTT | ACAATGTCTC | ATTGTAGTCT | 660 |
| GTCTTCAACT | ATTTTATCCA | AAATAAACCT | CCAGAAGGAA | AAAAAAAAA | AAAAAA | 716 |

(2) INFORMATION FOR SEQ ID NO:4:

(i) SEQUENCE CHARACTERISTICS:
(A) LENGTH: 104 amino acids
(B) TYPE: amino acid
(C) STRANDEDNESS: single
(D) TOPOLOGY: linear (i i) MOLECULE TYPE: protein (x i) SEQUENCE DESCRIPTION: SEQ ID NO:4:

| His | Glu | Asp | Lys | Asp | Asp | Ala | His | Tyr | Ala | Val | Gln | Ala | Arg | Arg | Ser |
| 1 | | | | 5 | | | | | 10 | | | | | 15 | |
| Arg | Ser | Ile | Thr | Arg | Lys | Arg | Lys | Arg | Glu | Asp | Ser | Ala | Pro | Pro | Ser |
| | | | 20 | | | | | 25 | | | | | 30 | | |
| Ser | Val | Ala | Arg | Ser | Gly | Ser | Cys | Ser | Arg | Thr | Pro | Arg | Asp | Val | Ser |
| | | | 35 | | | | 40 | | | | | 45 | | | |
| Gly | Leu | Arg | Asp | Val | Lys | Met | Val | Lys | Lys | Ala | Lys | Thr | Met | Met | Lys |
| | | | 50 | | | | 55 | | | | | 60 | | | |
| Asn | Ala | Gln | Lys | Lys | Met | Asn | Arg | Leu | Gly | Lys | Lys | Gly | Glu | Ala | Asp |
| 65 | | | | | 70 | | | | | 75 | | | | | 80 |
| Ile | His | Leu | Phe | Asp | Met | Lys | Pro | Lys | His | Leu | Leu | Ser | Gly | Lys | Arg |
| | | | | 85 | | | | | 90 | | | | | 95 | |
| Lys | Ala | Gly | Lys | Lys | Asp | Arg | Arg | | | | | | | | |
| | | | 100 | | | | | | | | | | | | |

(2) INFORMATION FOR SEQ ID NO:5:

(i) SEQUENCE CHARACTERISTICS:
(A) LENGTH: 13 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:5:

ACCACACATC TGA    13

( 2 ) INFORMATION FOR SEQ ID NO:6:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

TGTTGGGAAC AAG     13